United States Patent
Takemoto et al.

(10) Patent No.: US 8,476,473 B2
(45) Date of Patent: *Jul. 2, 2013

(54) COMPOUND, METHOD FOR PREPARING THE COMPOUND AND RESIST COMPOSITION CONTAINING THE COMPOUND

(75) Inventors: Ichiki Takemoto, Kawanishi (JP); Nobuo Ando, Toyonaka (JP); Mitsuhiro Hata, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 791 days.

This patent is subject to a terminal disclaimer.

(21) Appl. No.: 12/552,085

(22) Filed: Sep. 1, 2009

(65) Prior Publication Data
US 2010/0055609 A1 Mar. 4, 2010

(30) Foreign Application Priority Data
Sep. 2, 2008 (JP) .................................. 2008-225072

(51) Int. Cl.
 *C07C 69/63* (2006.01)
 *C07C 69/74* (2006.01)
(52) U.S. Cl.
 USPC ......................................... 560/227; 560/127
(58) Field of Classification Search
 USPC ........................................ 430/270.1; 560/227
 See application file for complete search history.

(56) References Cited

U.S. PATENT DOCUMENTS
6,762,007 B2 7/2004 Namba et al.
2003/0180663 A1 9/2003 Namba et al.

FOREIGN PATENT DOCUMENTS
JP 2003-280198 A 10/2003

*Primary Examiner* — Cynthia H. Kelly
*Assistant Examiner* — Connie P Johnson
(74) *Attorney, Agent, or Firm* — Birch, Stewart, Kolasch & Birch, LLP

(57) ABSTRACT

A compounds represented by the Formula (I) or the Formula (I').

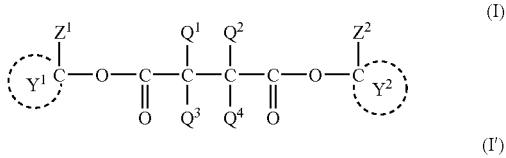

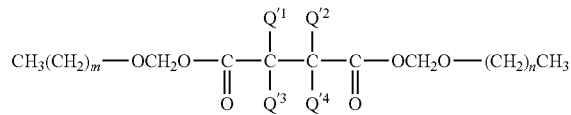

wherein $Z^1$ and $Z^2$ independently represent a hydrogen atom, a $C_1$ to $C_{12}$ alkyl group or a $C_3$ to $C_{12}$ cyclic saturated hydrocarbon group, provided that at least one of $Z^1$ and $Z^2$ represent a $C_1$ to $C_{12}$ alkyl group or a $C_3$ to $C_{12}$ cyclic saturated hydrocarbon group; rings $Y^1$ and $Y^2$ independently represents an optionally substituted $C_3$ to $C_{20}$ alicyclic hydrocarbon group; $Q^1$ to $Q^4$ and $Q'1$ to $Q'4$ independently represent a fluorine atom or a $C_1$ to $C_6$ perfluoroalkyl group; and m and n independently represent an integer of 0 to 5.

3 Claims, No Drawings

COMPOUND, METHOD FOR PREPARING THE COMPOUND AND RESIST COMPOSITION CONTAINING THE COMPOUND

BACKGROUND OF THE INVENTION

Field of the Invention

The present invention relates to a compound, a method for producing the compound and a resist composition containing the compound.

In chemically amplified positive resists, an acid generated in the exposed parts is diffused through subsequent heat treatment (post-exposure baking: PEB) and removes protective groups in a resin or the like, and acid is regenerated, so as to render the exposed parts of the resist alkali-soluble.

In chemically amplified negative resists, an acid generated in the exposed parts is diffused through PEB and acts on the cross-linker to cure a matrix resin in the exposed parts.

A method for dramatically accelerating an acid catalyst reaction by combining an acid amplification reaction, which involves the amplified generation of new acid through autocatalytic decomposition in the resist by the action of the acid, with a radiation-acid reaction, which involves the generation of acid in the resist through irradiation is proposed. Various acid amplifiers which are used in such a method are also proposed (for example, see Japanese Laid-open Patent Application No. 2003-280198).

Here, compounds having the structure shown in the following formula are disclosed as acid amplifiers included in resist compositions suitable for lithography involving the use of KrF excimer laser.

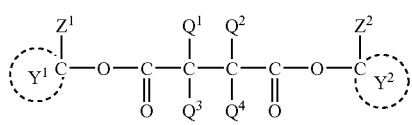
(I)

SUMMARY OF THE INVENTION

The present invention provides
<1> A compounds represented by the Formula (I) or the Formula (I').

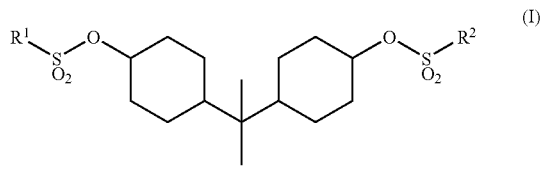
(I)

wherein $Z^1$ and $Z^2$ independently represent a hydrogen atom, a $C_1$ to $C_{12}$ alkyl group or a $C_3$ to $C_{12}$ cyclic saturated hydrocarbon group, provided that at least one of $Z^1$ and $Z^2$ represent a $C_1$ to $C_{12}$ alkyl group or a $C_3$ to $C_{12}$ cyclic saturated hydrocarbon group; rings $Y^1$ and $Y^2$ independently represents an optionally substituted $C_3$ to $C_{20}$ alicyclic hydrocarbon group; and $Q^1$ to $Q^4$ independently represent a fluorine atom or a $C_1$ to $C_6$ perfluoroalkyl group;

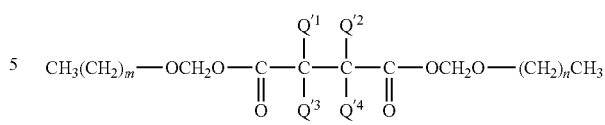
(I')

wherein $Q'^1$ to $Q'^4$ independently represent a fluorine atom or a $C_1$ to $C_6$ perfluoroalkyl group; m and n independently represent an integer of 0 to 5.

<2> The compound of <1>, wherein $Q^1$ to $Q^4$ and $Q'^1$ to $Q'^4$ are fluorine atoms.

<3> A method for producing a compound represented by the Formula (I) comprising a step of reacting a compound represented by the Formula (II) with a compound represented by the Formula (III) and a compound represented by the Formula (IV).

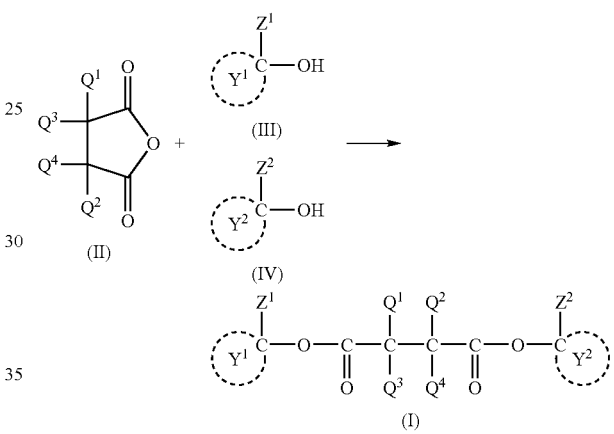

wherein $Z^1$, $Z^2$, ring $Y^1$, ring $Y^2$ and $Q^1$ to $Q^4$ are the same meaning of the above.

<4> A method for producing a compound represented by the Formula (I) comprising a step of reacting a compound represented by the Formula (V) with a compound represented by the Formula (III) and a compound represented by the Formula (VI).

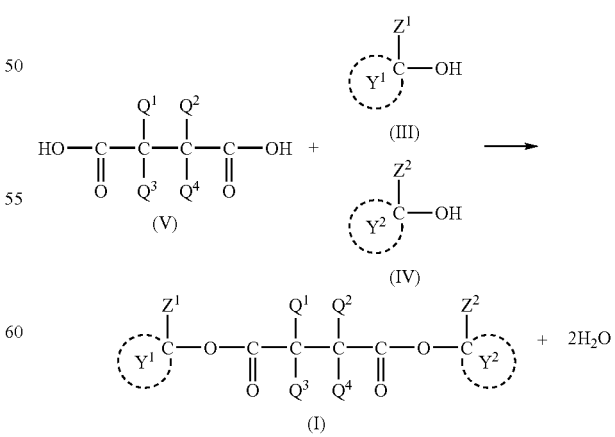

wherein $Z^1$, $Z^2$, ring $Y^1$, ring $Y^2$ and $Q^1$ to $Q^4$ are the same meaning of the above.

<5> A method for producing a compound represented by the Formula (I') comprising a step of reacting a compound represented by the Formula (V) with a compound represented by the Formula (VII) and a compound represented by the Formula (VIII).

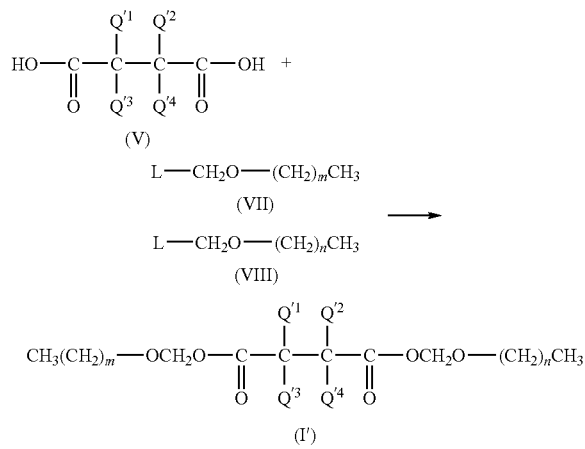

wherein $Q'^1$, $Q'^4$, m and n are the same meaning of the above.

<6> A resist composition comprising a compound of <1> or <2>, a resin which has an acid-labile group, is insoluble or poorly soluble in an alkali aqueous solution but rendered soluble in an alkali aqueous solution by the action of an acid; and an acid generator.

The compounds of the present invention make it possible to fully exploit autocatalytic reactions in which a strong acid is released anew through efficient decomposition by the action of the acid.

The method for producing the compounds of the invention also allows effective compounds to be efficiently produced.

Furthermore, the resist composition of the present invention makes it possible to provide a highly sensitive chemically amplified resist composition.

DETAILED DESCRIPTION OF THE PREFERRED EMBODIMENTS

A compound of the present invention is represented by the Formula (I) or (I'), hereinafter referred to as Compound (I) or (I').

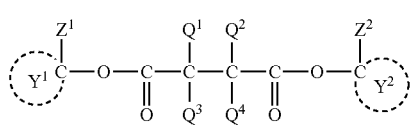

wherein $Z^1$ and $Z^2$ independently represent a hydrogen atom, a $C_1$ to $C_{12}$ alkyl group or a $C_3$ to $C_{12}$ cyclic saturated hydrocarbon group, provided that at least one of $Z^1$ and $Z^2$ represent a $C_1$ to $C_{12}$ alkyl group or a $C_3$ to $C_{12}$ cyclic saturated hydrocarbon group; rings $Y^1$ and $Y^2$ independently represents an optionally substituted $C_3$ to $C_{20}$ alicyclic hydrocarbon group; and $Q^1$ to $Q^4$ independently represent a fluorine atom or a $C_1$ to $C_6$ perfluoroalkyl group;

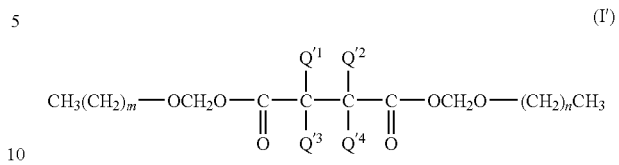

wherein $Q'^1$ to $Q'^4$ independently represent a fluorine atom or a $C_1$ to $C_6$ perfluoroalkyl group; and m and n independently represent an integer of 0 to 5.

Examples of the $C_1$ to $C_{12}$ alkyl group include methyl, ethyl, n-propyl, isopropyl, n-butyl, sec-butyl, tert-butyl, pentyl, hexyl, octyl, nonyl decyl undecyl, dodecyl and 2,2-dimethylhexyl groups.

Examples of the $C_3$ to $C_{12}$ cyclic saturated hydrocarbon include cyclopropyl, cyclobutyl, cyclopentyl, cyclohexyl, cycloheptyl, cycloocthyl, cyclononyl, cyclodecyl, cycloundecyl, cyclododecyl, norbornyl and adamantyl groups.

Examples of the $C_3$ to $C_{20}$ alicyclic hydrocarbon group include a divalent substituent which has bonds at any position of the compound represented by the formula below. Among these, a divalent substituent which has 2 bonds at the position represented by asterisk is preferable.

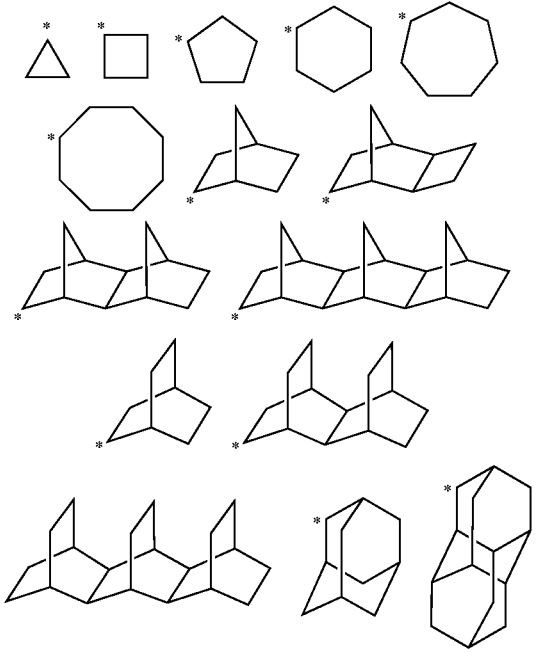

A substituent which may be substituted to an alicyclic hydrocarbon group is not limited to, and may be an inactive substituent to a reaction for the production of the Compound (I). Examples thereof include alkyl and alkoxyl groups. These substituents preferably have one to six carbon atoms.

The perfluoroalkyl group in $Q^1$, $Q^2$, $Q^3$ and $Q^4$ is not limited to, and a $C_1$ to $C_6$ perfluoroalkyl group is suitable. Examples of the perfluoroalkyl group include trifluoromethyl, pentafluoroethyl, heptafluoropropyl, nonafluorobutyl, perfluoropenthyl and perfluorohexyl groups.

$Z^1$ and $Z^2$ each independently is preferably methyl, ethyl, isopropyl, n-butyl, cyclopentyl or cyclohexyl group, and more preferably methyl, ethyl or isopropyl group. $Z^1$ and $Z^2$ are preferably the same groups.

The rings $Y^1$ and $Y^2$ each independently is preferably the following divalent substituent which has bonds at any position of the following compound and more preferably the following divalent substituent which has 2 bonds at the position represented by asterisk.

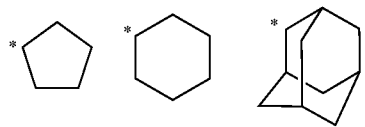

$Q^1$, $Q^2$, $Q^3$ and $Q^4$ each independently is preferably fluorine atom or trifloromethyl group, and more preferably fluorine atoms.

Examples of preferable Compounds (I) include a compound which is obtained by optionally combining these preferable substituents.

Examples of Compound (I) include the followings.

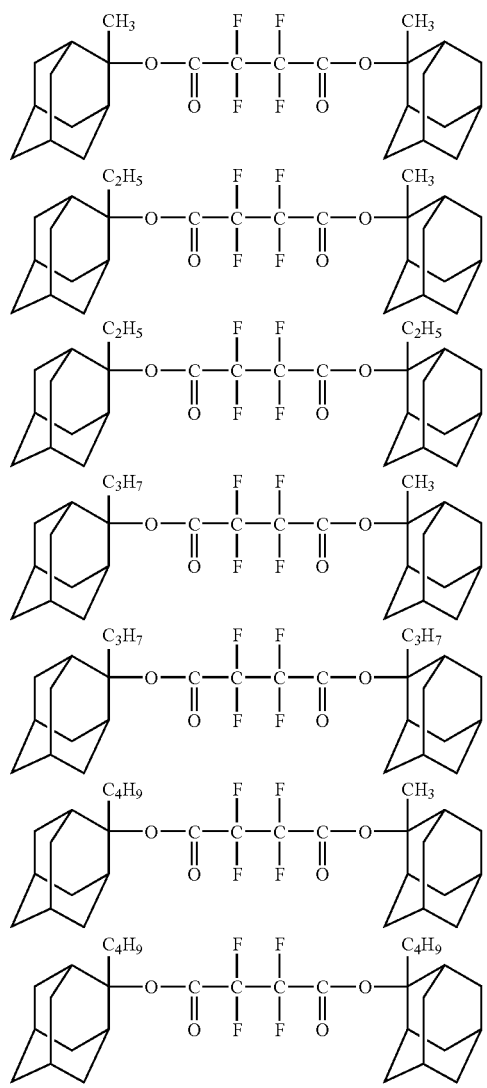

-continued

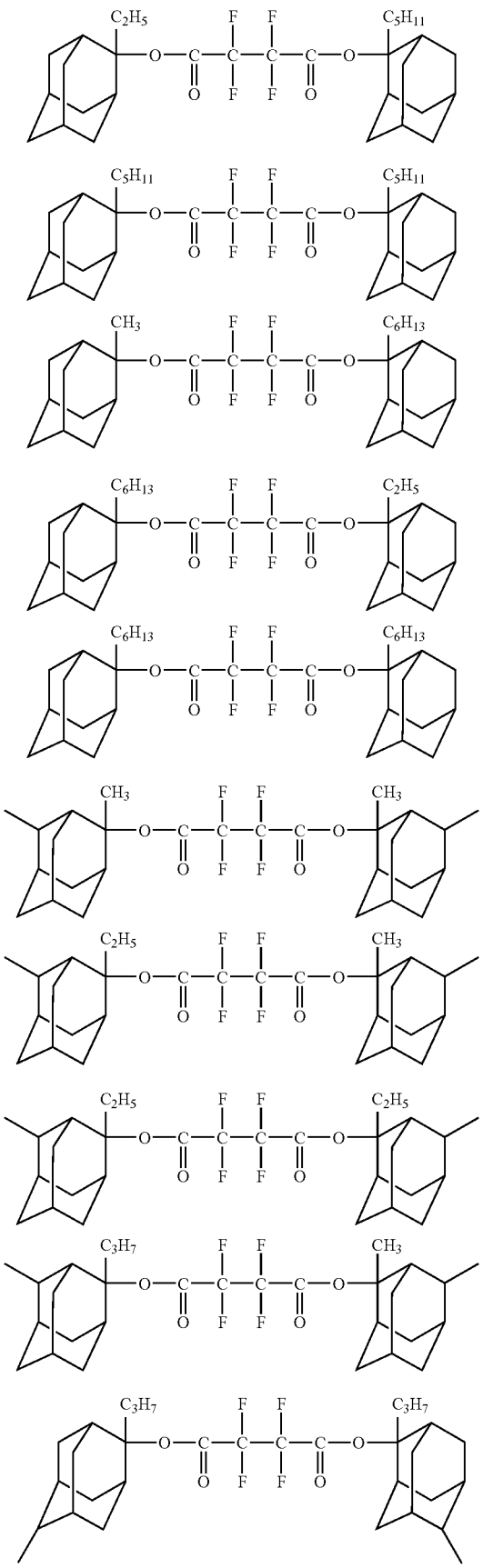

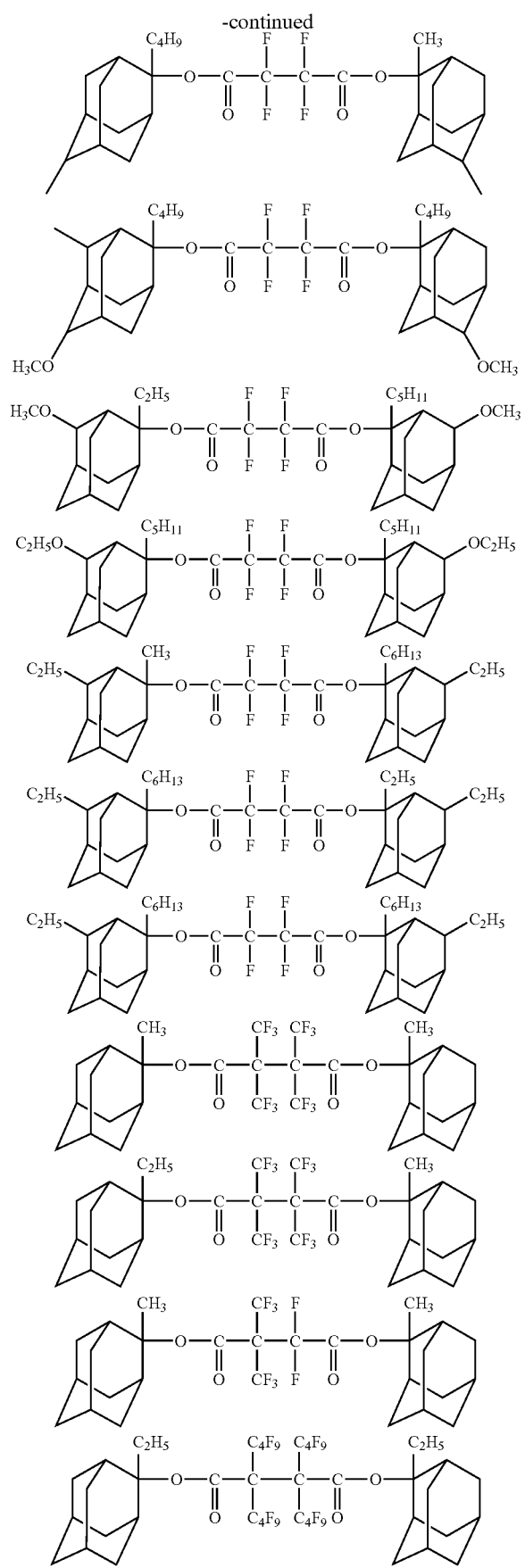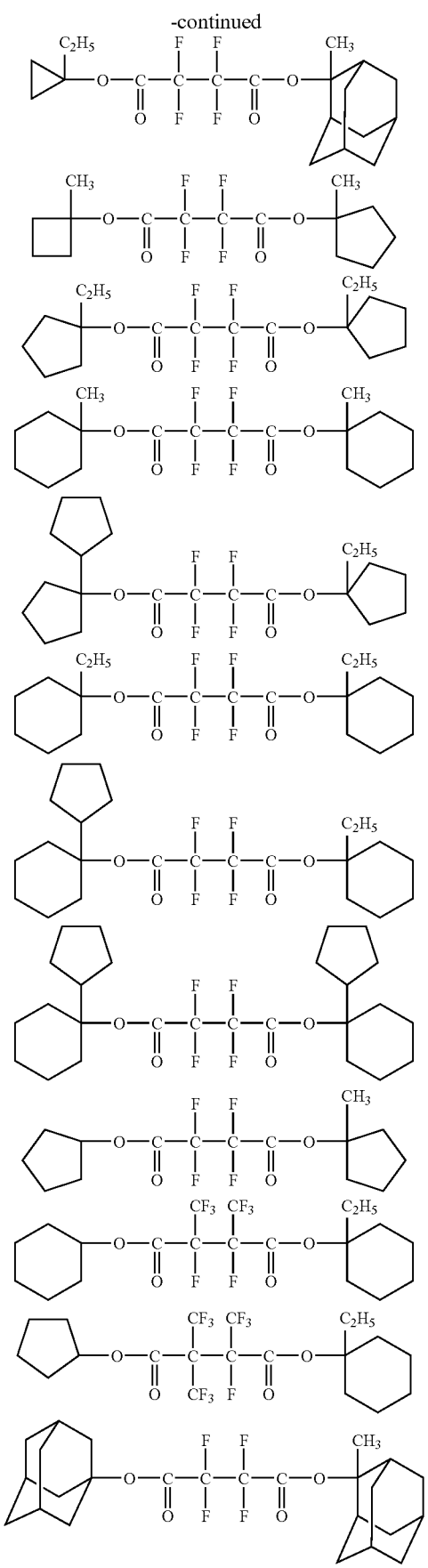

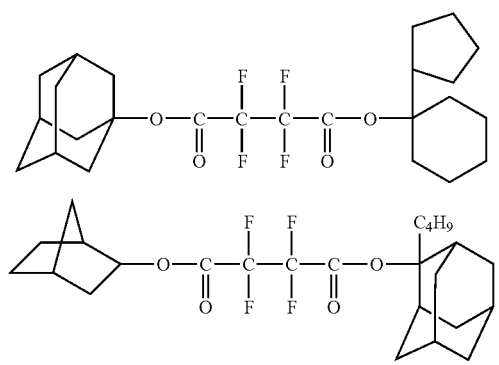

Examples of Compound (I') include the followings.

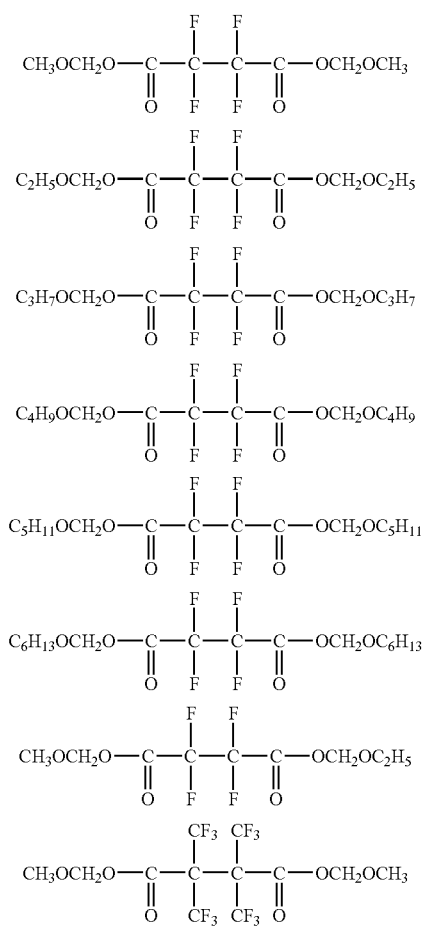

The Compound (I) can be produced by reacting a compound represented by the Formula (II) with a compound represented by the Formula (III) and a compound represented by the Formula (IV) as follows (hereinafter, simply referred to as REACTION (A)).

Also, the Compound (I) can be produced by dehydration-reacting a compound represented by the Formula (V) with a compound represented by the Formula (III) and a compound represented by the Formula (VI) as follows (hereinafter, simply referred to as REACTION (B)).

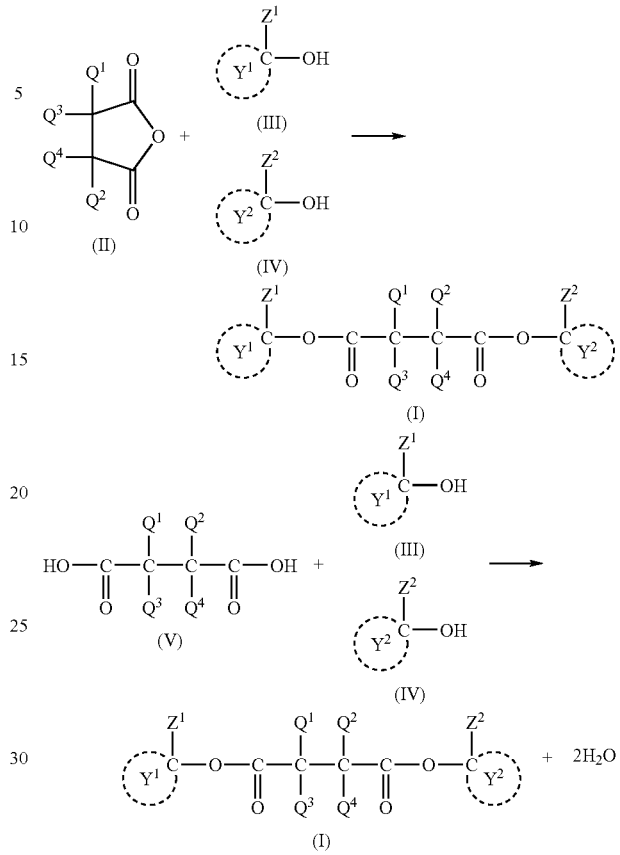

wherein $Z^1$, $Z^2$, ring $Y^1$, ring $Y^2$ and $Q^1$ to $Q^4$ are the same meaning of the above.

REACTION (A) and REACTION (B) can be carried out in the presence of a solvent that is inactive in the reaction, or in the absence of a solvent.

Examples of such solvents include hydrocarbons such as hexane, cyclohexane, and toluene; halogenated hydrocarbons such as methylene chloride, 1,2-dichloroethane, chloroform, carbon tetrachloride, and chlorobenzene; chain or cyclic ethers such as diethyl ether, dimethoxyethane, tetrahydrofuran, and dioxane; nitriles such as acetonitrile and benzonitrile; esters such as ethyl acetate; amides such as N,N-dimethyl formamide; ketones such as acetone and methyl ethyl ketone; nitro compounds such as nitromethane and nitrobenzene; and sulfur-containing compounds such as dimethyl sulfoxide and sulforane; and a mixtures of two or more of the above may be used.

REACTION (A) is usually conducted in the presence of a catalyst, and basic compounds, specifically, pyridine, triethylamine, dimethyl aniline, 4-dimethyl amino pyridine, etc., or a mixture thereof, are also preferred as catalysts REACTION (A) may also be carried out in the presence of a Lewis acid ($FeBr_3$, $AlBr_3$, etc.). The amount of the catalyst is usually a catalytic amount or more, and preferably a catalytic amount to 4 mole pre 1 mol of the compound represented by the Formula (II).

REACTION (B) is usually conducted in the presence of a dehydrating agent. Examples of dehydrating agents used when producing a Compound (I) by the reaction between the compound represented by Formula (V), and compounds represented by Formula (III) and Formula (IV) include dicyclohexylcarbodiimide (DCC), 1-alkyl-2-halopyridinium salts, 1,1-carbonyldiimidazole, bis(2-oxo-3-ozazolidinyl)phosphinic chloride, 1-ethyl-3-(3-dimethylaminopropyl)carbodiimide hydrochloride, di-2-pyridyl carbonate, di-2-pyridylthionocarbonate, and 6-methyl-2-nitrobenzoic anhydride/4-(dimethylamino)pyridine (catalyst). The amount of the dehydrating agent is usually 2 mol or more, and preferably 2 mole to 4 mole pre 1 mol of the compound represented by the Formula (V).

REACTION (A) can be carried out with about 0.1 to 10 mol of the compound represented by Formulas (III) and (IV) relative to 1 mol of the compound of Formula (II). REACTION (B) can be carried out with about 0.1 to 10 mol of the compound represented by Formulas (III) and (IV) relative to 1 mol of the compound of Formula (V).

When the Compound (I) is produced by the reaction between the compound represented by Formula (II), and compounds represented by Formula (III) and Formula (IV), the reaction temperature is usually −70 to 100° C., preferably −50 to 80° C., and more preferably about −20 to 50° C.

When the Compound (I) is produced by the reaction between the compound represented by Formula (V), and compounds represented by Formula (III) and Formula (IV), the reaction temperature is usually −50 to 200° C., preferably −20 to 150° C., and more preferably about −10 to 120° C. Within this temperature range, the reaction velocity will not decrease, and the reaction time will not be too long.

The reaction pressure is usually in the range of 0.01 to 10 MPa, and preferably normal pressure to 1 MPa absolute pressure.

The reaction time is usually in the range of 1 minute to 24 hours, and preferably 5 minutes to 12 hours.

The reaction product is preferably purified after completion of the reaction. A suitable method is preferably selected, for example, from common methods of separation and purification, such as filtration, concentration, crystallization, washing, recrystallization, distillation, and column chromatography, depending on the properties of the product, the type of impurities, and so forth.

The resulting compound can be identified using gas chromatography (GC), liquid chromatography (LC), gas chromatography-mass spectrometry (GC-MS), nuclear magnetic resonance (NMR), infrared spectroscopy (IR), a melting point analyzer, or the like.

The Compound (I') of the present invention can also be produced by a reaction between the compound represented by Formula (V), and the compounds represented by Formula (VII) and Formula (VIII), as shown below (hereinafter, simply referred to as REACTION (C)).

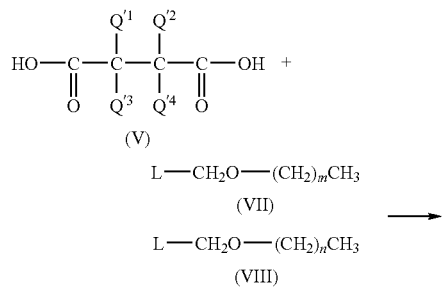

(V)

L—CH$_2$O—(CH$_2$)$_m$CH$_3$ (VII)

L—CH$_2$O—(CH$_2$)$_n$CH$_3$ (VIII)

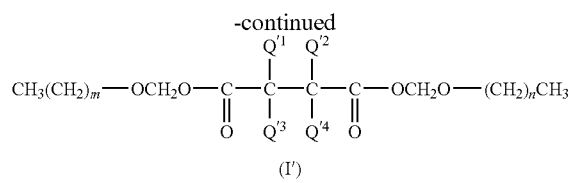

(I')

wherein $Q'^1$ to $Q'^4$, m, and n are the same meaning as defined above, and L represents a halogen atom.

REACTION (C) can be conducted in the presence or absence of an inert solvents for the reaction. Examples of inert solvents for the reaction include aprotic solvents such as dichloroethane, toluene, ethyl benzene, monochlorobenzene, diethyl ether, tetrahydrofuran, dioxane, acetone, methyl ethyl ketone, ethyl acetate, dimethyl sulfoxide and N,N-dimethyl formamide.

The reaction is preferably carried out while stirred at a temperature in the range from about −70° C. to 200° C., and preferably about −50° C. to 150° C.

A deacidifying agent is preferably used in the reaction. Examples of deacidifying agents include organic bases such as triethylamine and pyridine, or inorganic bases such as sodium hydroxide, potassium carbonate, and sodium hydride. The amount thereof may be an amount corresponding to the solvent, and is usually about 0.001 to about 5 mols, and preferably about 1 to 3 mols, per 1 mol of the compound of Formula (V).

Examples of halogen atoms L in Formula (VII) and Formula (VIII) include fluorine, chlorine, bromine, and iodine atoms, and is preferably chlorine, bromine, or iodine atom, and more preferably chlorine or bromine atom.

The Compound (I) and Compound (I') of the present invention function as so-called acid amplifiers, which are decomposed by acid to generate strong acid on their own. They are therefore preferably blended with a resist composition. In such cases, the Compound (I) and Compound (I') may be used individually or in combinations of two or more.

Examples of such resist compositions include those containing a resin which has an acid-labile group, is insoluble or poorly soluble in alkali aqueous solution but rendered soluble in alkali aqueous solution by the action of an acid, and an acid generator.

Here, the resins are not limited, as long as they are resins having such properties, and any of known resins in the field can be used. Examples thereof include the known resins disclosed in Japanese Laid-open Patent Application Nos. 2007-197718, 2005-331918, 2005-352466, and 2005-097516.

The acid generator is also not limited, and any of known acid generators in the field can also be used. Those that are compatible with the above resins are preferable.

Examples thereof include the known acid generators disclosed in Japanese Laid-open Patent Application Nos. 2008-056668, 2007-161707, and 2008-106045.

The amount of the acid generator is usually about 0.1 to 50 parts by weight, preferably about 0.1 to 20 parts by weight, and more preferably about 1 to 10 parts by weight, per 100 parts by weight of the resin, based on the total amount of solids. The use of the acid generator in this range will allow patterns to be adequately formed, and will result in a homogenous solution and good storage stability.

The Compound (I) or Compound (I') is also usually used in an amount of about 0.5 to 30 parts by weight, preferably 0.5 to 10 parts by weight, and more preferably 1 to 5 parts by weight, per 100 parts by weight of the resin. The use thereof in this range will accelerate the acid catalyst reaction in the resist composition, and thereby increase sensitivity to allow a good resist pattern to be obtained.

Such a resist composition may include additives that are well known in the field, such as quenchers, sensitizers, dissolution inhibitors, other resins, surfactants, stabilizers, and dyes, in addition to the above components.

This resist composition can also be used in lithographic processes involving the use of various light sources that are employed in the field, including those which emit laser light in the ultraviolent region, such as KrF excimer lasers (wavelength 248 nm), ArF excimer lasers (wavelength 193 nm), and $F_2$ lasers (wavelength 157 nm), and those which emit harmonic laser light in the infrared region or vacuum ultraviolet region by converting the wavelength of laser light from solid laser light sources (such as YAG or semiconductor lasers). Resist compositions that are suitable for lithography using ArF excimer lasers in particular can be provided.

EXAMPLES

The present invention will be described more specifically by way of examples, which are not construed to limit the scope of the present invention.

All percentages and parts expressing the content or amounts used in the examples and comparative examples are based on weight, unless otherwise specified.

Example 1

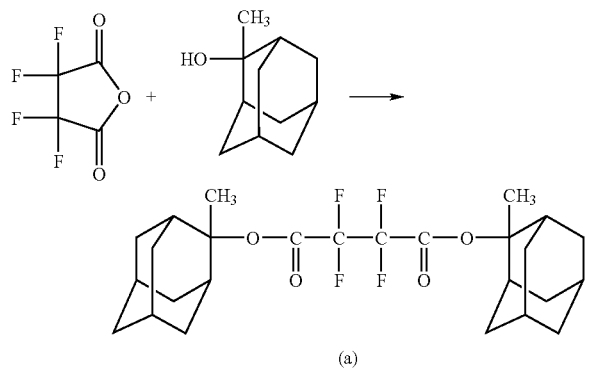

(a)

2-Methyl-2-adamantanol (9.71 g; 58 mmol), triethylamine (7.06 g; 70 mmol), and 4-dimethylaminopyridine (1.43 g; 12 mmol) were dissolved in anhydrous tetrahydrofuran (97.1 g; THF) to prepare a solution. A THF solution prepared by mixing tetrafluorosuccinic anhydride (10.0 g; 58 mmol) with THF (20.0 g) was added in the form of drops at 5° C. or less to the above solution.

The resultant solution was stirred for 3 hours at 5° C. or less. The reaction solution was concentrated at reduced pressure. The obtained residue was diluted with ethyl acetate, and mixed with 5% hydrochloric acid. The organic layer was separated and was washed with ion-exchanged water. The organic layer was dried over magnesium sulfate and then concentrated to give a crude product (20 g).

The crude product (11 g) was purified by silica gel chromatography (chloroform development) to give a compound represented by the above-mentioned formula (a) (5.37 g; yield 34.6%). This compound is designated A1.

$^1$H-NMR(CDCl$_3$): δ=2.35 (4H, s), 2.06-2.04 (4H), 1.90-1.78 (12H), 1.73 (4H, s), 1.69 (6H, s), 1.62-1.59 (4H)

$^{19}$F-NMR(CDCl$_3$): δ=−115.1

$^{13}$C-NMR(CDCl$_3$): δ=157.92 (t), 110.27 (t), 108.17 (t), 106.07 (t), 94.00, 37.90, 36.14, 34.61, 32.62, 27.12, 26.37, 21.93

FD-MS: 486 (M$^+$)

Example 2

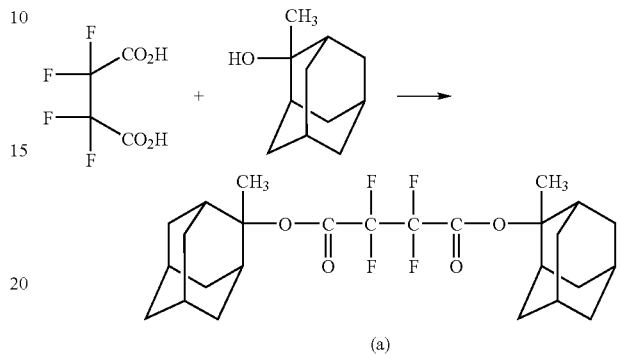

(a)

A chloroform solution prepared by mixing tetraflurosuccinic acid (0.25 g; 1.3 mmol) with chloroform (2.38 g) was stirred at room temperature, and a solution prepared by dissolving 2-methyl-2-adamantanol (0.44 g; 2.6 mmol) and 4-dimethylaminopyridine (0.32 g; 2.6 mmol) in chloroform (8 g) was added in the form of drops to the chloroform solution. Dicyclohexyl carbodiimide (0.54 g; 2.6 mmol) was added over a period of 5 minutes at room temperature to the resultant solution.

The resultant solution was stirred for 3 hours at room temperature. The reaction solution was concentrated at reduced pressure. The obtained residue was diluted with ethyl acetate, and mixed with 5% hydrochloric acid. The organic layer was separated and was washed with ion-exchanged water. The organic layer was dried over magnesium sulfate and then concentrated to give a crude product (1.3 g).

The crude product (1.3 g) was purified by silica gel chromatography (chloroform development) to give a compound represented by the above-mentioned formula (a) (0.29 g; yield 45.0%). This obtained compound has NMR spectrum corresponding to that of the compound A1.

Example 3

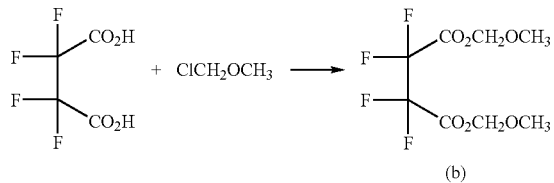

(b)

Tetraflurosuccinic acid (5.0 g; 26.3 mmol) was dissolved in anhydrous THF (40 g). Chloromethyl methyl ether (8.5 g, 105.5 mmol) was poured into this solution and the resultant solution was stirred under ice cooling. A solution prepared by dissolving triethylamine (10.6 g; 104.8 mmol), and 4-dimethylaminopyridine (0.6 g; 4.9 mmol) in anhydrous THF (20 g) was added in the form of drops at 4° C. to 27° C. to the above solution.

The resultant solution was stirred for 4 hours at room temperature. The reaction solution was extracted with 2% solution of sodium bicarbonate (300 g) and chloroform. The organic layer was separated and was washed with ion-exchanged water. The organic layer was dried over magnesium sulfate and then concentrated to give a compound represented by the above-mentioned formula (b) (3.3 g, yield 45.1%). This compound is designated A2.

$^1$H-NMR(CDCl$_3$): δ=3.55 (6H, s), 5.48 (4H, s)

$^{19}$F-NMR(CDCl$_3$): δ=−116.5

$^{13}$C-NMR(CDCl$_3$): δ=158.97 (t), 107.92 (m), 93.83, 58.40
FD-MS: 301 (M+Na)$^+$

Example 4

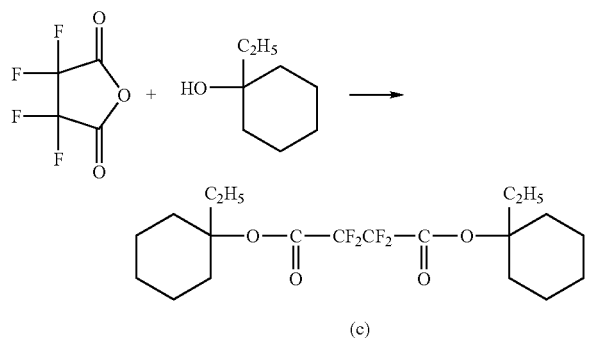

(c)

1-Ethylcyclohexanol (7.0 g, 58.2 mmol), triethylamine (6.5 g, 64.2 mmol) and 4-dimethylaminopyridine (0.7 g, 5.7 mmol) were dissolved in anhydrous THF (35 g), and the obtained solution was stirred under ice colling. A solution prepared by dissolving tetrafluorosuccinic anhydride (5.0 g; 29.1 mmol) in THF (10.0 g) was added in the form of drops at 10° C. to 27° C. to the above solution.

The resultant solution was stirred for one night at room temperature. The reaction solution was diluted with ethyl acetate (150 ml) and ion-exchanged water (200 ml). The organic layer was separated and was washed with ion-exchanged water. The organic layer was dried over magnesium sulfate and then concentrated to give a crude product (7.2 g). The crude product was purified by silica gel chromatography (hexane/ethyl acetate development) to give a compound represented by the above-mentioned formula (c) (1.5 g; yield 12.6%). This compound is designated A3.

$^1$H-NMR(CDCl$_3$): δ=2.29-2.26 (4H), 1.98 (4H, q, J-7.6z), 1.66-1.22 (16H), 0.88 (6H, t, J=7.6 Hz)

$^{19}$F-NMR(CDCl$_3$): δ=−114.5

Example 5

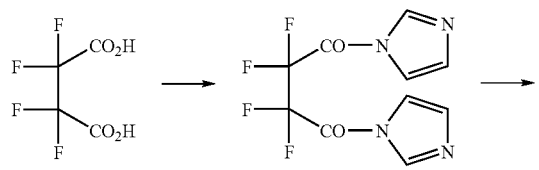

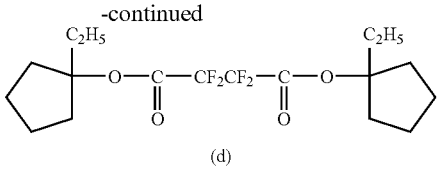

(d)

1,1'-Carbonyldiimidazole (27.19 g, 167.7 mmol) was dissolved in anhydrous THF (200 ml). A solution prepared by dissolving tetrafluorosuccinic acid (15.94 g; 83.9 mmol) in anhydrous THF (140 ml) was added in the form of drops to the above solution at 23° C. to 32° C. over a period of 10 minutes.

The resultant solution was stirred for 3 hours at room temperature. A solution prepared by dissolving 1-ethylcyclopentanol (16.56 g, 146.8 mmol) in anhydrous THF (16 ml) was added in the form of drops to the above solution at room temperature over a period of 5 minutes. The resultant solution was heated to reflux for 14 hours. After being cooled, the reaction solution was concentrated and residue was purified by alumina chromatography (hexane/ethyl acetate development) to give a compound represented by the above-mentioned formula (d) (8.42 g; yield 15.0%). This compound is designated A4.

$^1$H-NMR(CDCl$_3$): δ=2.23-2.18 (4H), 2.05 (4H, q, J=7.7 Hz), 1.80-1.62 (12H), 0.92 (6H, t, J=7.7 Hz)

$^{13}$C-NMR(CDCl$_3$): δ=158.32, 110.41-105.69, 100.06, 36, 73, 29.45, 8.39

$^{19}$F-NMR(CDCl$_3$): δ=−115.5

Example 6

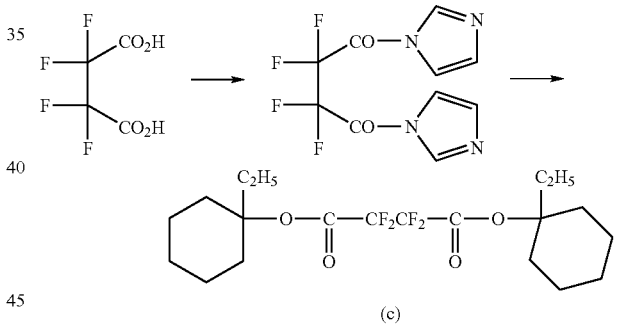

(c)

1,1'-Carbonyldiimidazole (24.36 g, 150.0 mmol) was dissolved in anhydrous THF (120 ml). A solution prepared by dissolving tetrafluorosuccinic acid (14.25 g; 75.0 mmol) in anhydrous THF (75 ml) was added in the form of drops to the above solution at 23° C. to 30° C. over a period of 10 minutes.

The resultant solution was stirred for 3 hours at room temperature. A solution prepared by dissolving 1-ethylcyclohexanol (18.54 g, 144.6 mmol) in anhydrous THF (20 ml) was added in the form of drops to the above solution at room temperature over a period of 5 minutes. To the resultant solution, 4-dimethylaminopilidine (20.16 g, 165.0 mmol) was added, and the resultant solution was heated to reflux for 23 hours. After being cooled, the reaction solution was distilled with pure water, and extracted with ethyl acetate. The organic layer was washed with saturated saline, and was dried over anhydrous sodium sulfate and then concentrated. The obtained residue was purified by silica gel chromatography (eluent: hexane/ethyl acetate) to give a compound represented by the above-mentioned formula (c) (33.6 g; yield 56.6%).

$^1$H-NMR(CDCl$_3$): δ=2.29-2.26 (4H), 1.98 (4H, q, J=7.6 Hz), 1.66-1.22 (16H), 0.88 (6H, t, J=7.6 Hz)
$^{13}$C-NMR(CDCl$_3$): δ=158.72, 110.53-105.80, 91.35, 33.73, 30.14, 25.21, 21.44, 7.05
$^{19}$F-NMR(CDCl$_3$): δ=−114.5
LC-MS: 433.1 ([M+Na]$^+$, Exact Mass=410.21)

The LC-MS analysis was preformed under following conditions:
LC apparatus: Agilent 1100
Column ODS A-210EC
Eluent: Eluent A; water
Eluent B: acetonitrile, The concentration ratio of Eluent B/Eluent A in Eluent was followed.

At 0 minute, the ratio Eluent B/Eluent A was 30/70, and then the ratio of Eluent B was increased up to a ratio of 100/0 at a constant rate, and reached to a ratio of 100/0 at 50 minutes, and then the ratio of 100/0 was maintained to 60 minutes.
Flow rate: 0.5 ml/min
MS apparatus: HP LC/MSD 6130
Ionization: ESI$^+$
Ionization promoter: 0.5 mM NaCl/(water:methanol=1:1)

The following monomers were used in the following Resin Synthesis Example 1.

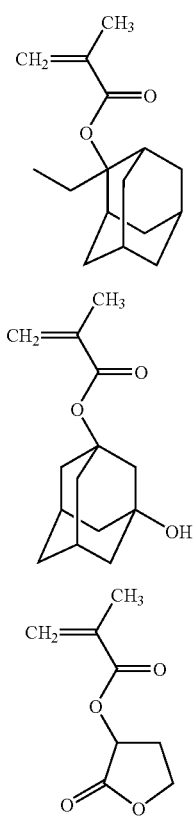

Resin Synthesis Example 1

Resin R1

24.36 parts of methyl isobutyl ketone was introduced into a four-neck flask equipped with a thermometer and a reflux tube, and was bubbled with nitrogen gas for 30 minutes, and then, was heated up to 72° C. under nitrogen sealed. 16.20 parts of monomer A, 11.56 parts of monomer B, 8.32 parts of monomer C, 0.27 parts of azobisisobutyronitrile, 1.22 parts of azobis-2,4-dimethyl valeronitrile and 29.77 parts of methyl isobutyl ketone were mixed, giving a solution. The solution was added in the form of drops to the four-neck flask over a period of 2 hours while keeping 72° C. After being added, it was kept at 72° C. for 5 hours. After being cooled, the reaction solution was diluted by adding 39.69 parts of methyl isobutyl ketone. The obtained mixture was poured into a mixture of 469 parts of methanol while stirred, and the precipitated resin was collected by filtration. The filtered resin was introduced into 235 parts of methanol, and the mixture was stirred, and then the resin was collected by filtration. These operations of introducing, stirring and filtering for the obtained resin were repeated two more times. The resin was then dried at reduced pressure, giving 22.7 parts of resin. This resin is designated Resin R1. Yield: 76%, Mw: 10124, Mw/Mn: 1.4.

Resin Synthesis Example 2

Resin R2

59.6 g (0.24 mol) of 2-ethyl-2-adamantyl metacrylate and 90.8 g (0.56 mol) of p-acetoxystyrene were dissolved in 265 g of isopropanol, which was heated at 75° C. under nitrogen atmosphere. 11.05 g (0.048 mol) of a radical initiator, dimethyl 2,2-azobis(2-methylpropionate) was dissolved in 22.11 g of isopropanol, and added in the form of drops to the above solution. The reaction solution was heated to reflux for 12 hours. After being cooled, the reaction solution was poured into a large amount of methanol, and the precipitated resin was collected by filtration. 250 g of the copolymer of 2-ethyl-2-adamantyl metacrylate and p-acetoxystyrene was obtained (contained methanol).

250 g of the obtained copolymer and 10.3 g (0.084 mol) of 4-dimethylaminopyridine were added to 202 g of methanol, and were heated to reflux for 20 hours. After being cooled, the reaction solution was neutralized with 7.6 g (0.126 mol) of glacial acetic acid, and was poured into large amount of water to precipitate. The operation, in which the precipitated resin was collected by filtration, was dissolved in acetone, and was poured into large amount of water to precipitate, were repeated three more times to purify. 102.8 g of the copolymer of 2-ethyl-2-adamantyl metacrylate and p-hydroxystyrene was obtained. The weight-average molecular weight thereof was about 8200 (GPC analysis: equivalent to polystylene), and ratio of the structural unit derived from 2-ethyl-2-adamantyl metacrylate and that derived from p-hydroxystyrene in the copolymer was about 30:70 (the structural unit derived from 2-ethyl-2-adamantyl metacrylate:the structural unit derived from p-hydroxystyrene, C$^{13}$ MNR measurement). This resin is designated Resin R2.

Example 7 to 11 and Comparative Example 1

Preparation of Resist Composition

<Resin>
Resin R1
Resin R2
<Acid Generator>
Acid Generator B1: Triphenylsulfonium 4-oxo-1-adamantyloxycarbonyl fluoromethanesulfonate, which was synthesized according to a method described in Japanese Laid-open Patent Application No. 2007-224008.

<Cross-Linker>

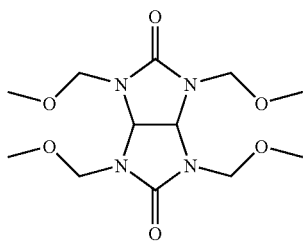

<Quencher>
Quencher Q1: 2,6-diisopropyl aniline

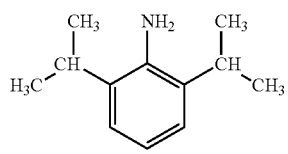

Quencher Q2: tetrabutyl ammonium hydroxide

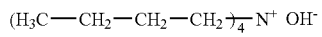

<Solvent>

| Solvent 1: | |
| --- | --- |
| Propylene glycol monomethyl ether | 450 parts |
| Propylene glycol monomethyl ether acetate | 40 parts |
| γ-butyrolactone | 5 parts |
| Solvent 2: | |
| Propylene glycol monomethyl ether | 240 parts |
| 2-heptanone | 35 parts |
| Propylene glycol monomethyl ether acetate | 20 parts |
| γ-butyrolactone | 3 parts |

<Acid Amplifier>
A1
A2
A3
A4

The ingredients shown in Table 1 were mixed and dissolved, and were furthermore filtered with a fluororesin filter having a pore diameter of 0.2 μm to prepare resist compositions.

TABLE 1

| Ex. No. | Resist | Resin (parts) | Acid Generator (parts) | Quencher (parts) | Acid amplifier (parts) | Solvent |
| --- | --- | --- | --- | --- | --- | --- |
| Ex. 7 | Composition 1 | R2/10 | B1/1.5 | Q1/Q2 = 0.075/0.005 | A1/0.2 | Solvent 1 |
| Ex. 8 | Composition 2 | R2/10 | B1/1.5 | Q1/Q2 = 0.075/0.005 | A2/0.1 | Solvent 1 |
| Ex. 9 | Composition 3 | R1/10 | B1/0.6 | Q1 = 0.01 | A1/0.6 | Solvent 2 |
| Ex. 10 | Composition 4 | R2/10 | B1/1.5 | Q1/Q2 = 0.075/0.005 | A3/0.15 | Solvent 1 |
| Ex. 11 | Composition 5 | R2/10 | B1/1.5 | Q1/Q2 = 0.075/0.005 | A4/0.15 | Solvent 1 |
| Comp. Ex. 1 | Composition 6 | R2/10 | B1/1.5 | Q1/Q2 = 0.075/0.005 | — | Solvent 1 |

Note:
Composition 3 contains further 0.2 parts of a cross-linker.

Examples 12, 13 and Comparative Example 2

A silicon wafers were baked for 60 seconds at 90° C. using hexamethyl disilazane on a direct hot plate. The above resist compositions shown in Table 1 were then applied thereon by spin coating to a dry film thickness of 0.06 μm, respectively.

The wafers were then pre-baked for 60 sec on a direct hot plate at the temperatures given in the "PB" column in Table 2.

Line and space patterns were then exposed through stepwise changes in exposure quantity using an electron beam lithograph apparatus (Hitachi, Ltd., HL-800D 50 KeV) on the wafers on which the resist film had thus been formed.

The exposure was followed by 60 seconds of post-exposure baking on a hot plate at the temperatures given in the "PEB" column in Table 1.

This was followed by 60 seconds of puddle development with 2.38 wt % tetramethylammonium hydroxide aqueous solution.

Table 2 gives the results of observations with scanning electron microscopy of the resulting pattern formed on the silicon substrate.

Effective sensitivity: It was represented as the exposure amount at which a 0.08 μm line and space pattern resolved to 1:1.

Resolution: It was represented as the minimum size of line and space pattern resolving at the exposure amount of the effective sensitivity.

TABLE 2

| Ex. No. | Resist No. | PB | PEB | Effective sensitivity (μC) | Resolution (nm) |
| --- | --- | --- | --- | --- | --- |
| Ex. 12 | Composition 1 | 110° C. | 100° C. | 26 | 60 |
| Ex. 13 | Composition 2 | 110° C. | 100° C. | 24 | 60 |
| Comp. Ex. 2 | Composition 6 | 110° C. | 100° C. | 34 | 60 |

Example 14

A resist pattern is produced in the same manner as in Example 12 except that the resist composition 3 is used instead of the resist composition 1.

Example 15

A resist pattern is produced in the same manner as in Example 12 except that the resist composition 4 is used instead of the resist composition 1.

Example 16

A resist pattern is produced in the same manner as in Example 12 except that the resist composition 5 is used instead of the resist composition 1.

Example 17

"ARC-29A-8" which is a composition for an organic antireflective film, by Brewer, Ltd., was applied onto silicon wafers and baked for 60 seconds at 205° C. to form a 78 nm thick organic antireflective film.

The above resist composition 3 was then applied thereon by spin coating to a dry film thickness of 0.08 μm.

The wafers were then pre-baked for 60 sec on a direct hot plate at 90° C.

On the wafers on which resist films had thus been formed were then exposed overall using an ArF excimer stepper ("FPA5000-AS3" by Canon: NA=0.75, 2/3 annular).

Line and space patterns were then exposed through a mask having 1:1 line and space patterns (100 nm of line width) using an ArF excimer stepper ("FPA5000-AS3" by Canon: NA=0.75, 2/3 annular) on the wafers on which resist films had thus been formed.

The exposure was followed by 60 seconds of post-exposure baking on a hot plate at 105° C.

This was followed by 60 sec of puddle development with 2.38 wt % tetramethylammonium hydroxide aqueous solution.

The wafers were then hard-baked for 60 sec at 170° C.

Thus obtained line and space patterns were observed with a scanning electron microscopy, and confirmed that the resulting pattern is excellent and fineness.

According to the compounds of the present invention, the chemically-amplified resist having high sensitivity can be obtained.

This application claims priority to Japanese Patent Application No. 2008-225072. The entire disclosure of Japanese Patent Application No. 2008-225072 is hereby incorporated herein by reference.

What is claimed is:

1. A compounds represented by the Formula (I) or the Formula (I'),

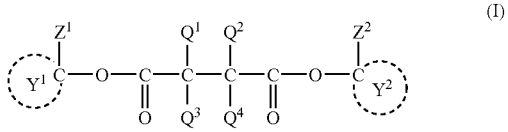

wherein $Z^1$ and $Z^2$ independently represent a hydrogen atom, a $C_1$ to $C_{12}$ alkyl group or a $C_3$ to $C_{12}$ cyclic saturated hydrocarbon group, provided that at least one of $Z^1$ and $Z^2$ represent a $C_1$ to $C_{12}$ alkyl group or a $C_3$ to $C_{12}$ cyclic saturated hydrocarbon group; rings $Y^1$ and $Y^2$ independently represents an optionally substituted $C_3$ to $C_{20}$ alicyclic hydrocarbon group; and $Q^1$ to $Q^4$ independently represent a fluorine atom or a $C_1$ to $C_6$ perfluoroalkyl group;

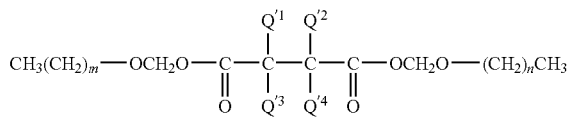

wherein $Q'^1$ to $Q'^4$ independently represent a fluorine atom or a $C_1$ to $C_6$ perfluoroalkyl group; and m and n independently represent an integer of 0 to 5.

2. The compound of claim 1, wherein $Q^1$ to $Q^4$ and $Q'^1$ to $Q'^4$ are fluorine atoms.

3. A resist composition comprising a compound of claim 1 or 2, a resin which has an acid-labile group, is insoluble or poorly soluble in an alkali aqueous solution but rendered soluble in an alkali aqueous solution by the action of an acid; and an acid generator.

* * * * *